(12) United States Patent
Zhang et al.

(10) Patent No.: US 9,610,375 B2
(45) Date of Patent: Apr. 4, 2017

(54) VOLATILE MATERIAL DISPENSER AND ITS HOUSING AND CARTRIDGE

(75) Inventors: Hua Zhang, Shanghai (CN); Jiajia Li, Shanghai (CN)

(73) Assignee: S.C. JOHNSON & SON, INC., Racine, WI (US)

(*) Notice: Subject to any disclaimer, the term of this patent is extended or adjusted under 35 U.S.C. 154(b) by 445 days.

(21) Appl. No.: 13/696,122

(22) PCT Filed: Apr. 27, 2011

(86) PCT No.: PCT/CN2011/073393
§ 371 (c)(1),
(2), (4) Date: Nov. 5, 2012

(87) PCT Pub. No.: WO2011/140917
PCT Pub. Date: Nov. 17, 2011

(65) Prior Publication Data
US 2013/0056550 A1    Mar. 7, 2013

(30) Foreign Application Priority Data
May 10, 2010    (CN) .................... 2010 2 0184271 U (51) Int. Cl.
*A61L 9/04*    (2006.01)
*A61L 9/12*    (2006.01)

(52) U.S. Cl.
CPC ........... *A61L 9/12* (2013.01); *A61L 2209/133* (2013.01)

(58) Field of Classification Search
CPC .... A61L 9/12; A61L 2209/133; A01M 1/2055
(Continued)

(56) References Cited

U.S. PATENT DOCUMENTS

| | | |
|---|---|---|
| 2,247,600 A | 7/1941 | Brennen et al. |
| 2,642,310 A | 6/1953 | Meek et al. |

(Continued)

FOREIGN PATENT DOCUMENTS

| | | |
|---|---|---|
| CN | 2736289 Y | 10/2005 |
| EP | 3003 | 7/1979 |

(Continued)

*Primary Examiner* — Jason Boeckmann (57) ABSTRACT

A volatile material dispenser (100) and its housing and cartridge (600; 700) are disclosed. The housing for the volatile material dispenser (100) comprises a bottom plate (200; 200'), a covering plate (300) and a chamber defined therebetween for receiving a cartridge (600; 700), and the housing further comprises a regulating plate (400) movably mounted to the covering plate (300). The covering plate (300) and the regulating plate (400) each have one bored portion and one non-bore portion. The bored portion (420) and the non-bore portion (410) of the regulating plate (400) each occupy a half of the regulating plate (400). The regulating plate (400) is movable between an open position and a closed position with respect to the covering plate (300). The bored portion (320) of the covering plate (300) is aligned with the bored portion (420) of the regulating plate (400) in the open position, and the bored portion (320) of the covering plate (300) is covered by the non-bore portion (410) of the regulating plate (400) in the closed position. The chamber is provided with a fixing element capable of fixing the cartridge (600; 700) in place. The advantages of the present invention lie in that the dispensing of the dispenser (100) can be controlled more precisely.

21 Claims, 5 Drawing Sheets

(58) Field of Classification Search
USPC .................................... 239/57–60, 51.5, 49
See application file for complete search history.

(56) References Cited

U.S. PATENT DOCUMENTS

| | | | |
|---|---|---|---|
| 2,657,090 A | | 10/1953 | Meek |
| 2,765,194 A | * | 10/1956 | Theodore ............ A01M 1/2055 239/59 |
| 3,976,246 A | | 8/1976 | Hauri et al. |
| 3,991,915 A | | 11/1976 | Kinnavy |
| 4,040,568 A | | 8/1977 | Mason, Jr. et al. |
| 4,067,692 A | | 1/1978 | Farris |
| 4,154,398 A | | 5/1979 | Gualandi |
| 4,219,145 A | | 8/1980 | Jaeschke et al. |
| 4,248,380 A | | 2/1981 | Lee et al. |
| 4,258,004 A | | 3/1981 | Valenzona et al. |
| 4,258,874 A | | 3/1981 | Webinger et al. |
| 4,277,014 A | | 7/1981 | Webinger |
| 4,301,949 A | | 11/1981 | Palson et al. |
| 4,306,679 A | | 12/1981 | Dusek et al. |
| 4,339,079 A | | 7/1982 | Sato et al. |
| 4,356,969 A | | 11/1982 | Obermayer et al. |
| 4,361,279 A | | 11/1982 | Beacham |
| 4,502,630 A | | 3/1985 | Haworth et al. |
| 4,512,933 A | | 4/1985 | Harden |
| 4,523,870 A | | 6/1985 | Spector |
| 4,583,686 A | | 4/1986 | Martens et al. |
| 4,630,775 A | | 12/1986 | Mandon et al. |
| 4,634,614 A | | 1/1987 | Holzner |
| 4,664,312 A | | 5/1987 | Bryson |
| 4,809,912 A | | 3/1989 | Santini |
| 4,849,606 A | | 7/1989 | Martens, III et al. |
| 4,865,816 A | | 9/1989 | Walz et al. |
| 4,878,615 A | | 11/1989 | Losi |
| 4,940,272 A | | 7/1990 | Weick |
| 4,947,578 A | | 8/1990 | Anderson et al. |
| 4,961,532 A | | 10/1990 | Tangney |
| 4,968,456 A | | 11/1990 | Muderlak et al. |
| 5,033,674 A | | 7/1991 | Smith |
| 5,115,975 A | | 5/1992 | Shilling |
| 5,145,604 A | | 9/1992 | Neumiller |
| 5,148,984 A | | 9/1992 | Bryson, Jr. et al. |
| 5,219,121 A | | 6/1993 | Fox et al. |
| 5,304,358 A | * | 4/1994 | Hoyt et al. .................... 422/305 |
| 5,314,669 A | | 5/1994 | Hamilton |
| 5,361,522 A | | 11/1994 | Green |
| 5,388,714 A | | 2/1995 | Zutler |
| 5,478,505 A | | 12/1995 | Mcelfresh et al. |
| 5,516,504 A | | 5/1996 | Tomlinson |
| 5,527,493 A | | 6/1996 | Mcelfresh et al. |
| 5,565,148 A | | 10/1996 | Pendergrass, Jr. |
| 5,651,522 A | | 7/1997 | Davis |
| 5,695,692 A | | 12/1997 | Kennedy |
| 5,782,409 A | | 7/1998 | Paul |
| 5,868,315 A | | 2/1999 | Chen |
| 5,898,475 A | | 4/1999 | Martin |
| 5,899,382 A | | 5/1999 | Hayes et al. |
| 6,029,901 A | | 2/2000 | Toy, II |
| 6,080,367 A | | 6/2000 | Lin |
| 6,085,989 A | | 7/2000 | Cox |
| 6,171,608 B1 | | 1/2001 | Schmitt et al. |
| 6,241,219 B1 | | 6/2001 | Logan et al. |
| 6,244,518 B1 | | 6/2001 | Pogue |
| 6,254,248 B1 | | 7/2001 | McAuley et al. |
| 6,254,836 B1 | | 7/2001 | Fry |
| 6,361,788 B1 | | 3/2002 | Antoni-Zimmermann et al. |
| 6,502,762 B2 | | 1/2003 | Tuttobene, Jr. |
| 6,551,560 B1 | | 4/2003 | Flashinski et al. |
| 6,607,434 B1 | | 8/2003 | Park |
| 6,610,254 B1 | | 8/2003 | Furner et al. |
| 6,631,852 B1 | | 10/2003 | O'Leary |
| 6,655,604 B2 | | 12/2003 | Tuttobene, Jr. |
| 6,746,521 B2 | | 6/2004 | Canfield |
| 6,767,521 B1 | | 7/2004 | Vogt et al. |
| 6,909,840 B2 | | 6/2005 | Harwig et al. |
| 7,036,800 B2 | | 5/2006 | Ellis |
| 7,070,172 B2 | | 7/2006 | Fabrega et al. |
| 7,152,809 B2 | | 12/2006 | Ketcha et al. |
| 7,344,729 B2 | | 3/2008 | Kemmis et al. |
| 7,503,675 B2 | | 3/2009 | Demarest et al. |
| 7,544,332 B2 | | 6/2009 | De Silva et al. |
| 7,833,492 B2 | * | 11/2010 | Schumacher ........ A01M 1/2033 422/124 |
| 7,887,826 B2 | | 2/2011 | Costa |
| 7,988,073 B2 | | 8/2011 | Ligney et al. |
| 8,005,349 B2 | | 8/2011 | Deflorian et al. |
| 8,020,785 B2 | | 9/2011 | Chao |
| 8,047,837 B2 | | 11/2011 | Furner et al. |
| 8,048,379 B2 | | 11/2011 | Sassoon |
| 8,096,486 B2 | | 1/2012 | Wang et al. |
| 8,119,150 B2 | | 2/2012 | Tamarkin et al. |
| 8,137,715 B2 | | 3/2012 | Shah et al. |
| 8,985,479 B2 | * | 3/2015 | Dobler ........................ 239/289 |
| 2003/0038133 A1 | | 2/2003 | Liu |
| 2003/0060350 A1 | | 3/2003 | Taylor et al. |
| 2005/0042245 A1 | | 2/2005 | Taranta et al. |
| 2005/0089502 A1 | | 4/2005 | Schansberg et al. |
| 2005/0127538 A1 | | 6/2005 | Fabrega et al. |
| 2006/0283970 A1 | * | 12/2006 | Faires ..................... A61L 9/048 239/6 |
| 2007/0051826 A1 | | 3/2007 | Schofield |
| 2007/0057086 A1 | | 3/2007 | Van Kippersluis |
| 2007/0075159 A1 | * | 4/2007 | Lin ............................... 239/60 |
| 2008/0023568 A1 | | 1/2008 | Weggelaar et al. |
| 2008/0095522 A1 | | 4/2008 | Deflorian et al. |
| 2008/0175913 A1 | | 7/2008 | Zhang et al. |
| 2008/0193640 A1 | | 8/2008 | Zhang et al. |
| 2008/0245890 A1 | | 10/2008 | Lockwood et al. |
| 2008/0257978 A1 | | 10/2008 | Marth et al. |
| 2008/0277415 A1 | | 11/2008 | Pirrie et al. |
| 2009/0010813 A1 | | 1/2009 | Wang et al. |
| 2009/0118367 A1 | | 5/2009 | Steward et al. |
| 2009/0163582 A1 | | 6/2009 | Wang et al. |
| 2009/0182040 A1 | | 7/2009 | Heger et al. |
| 2009/0212124 A1 | * | 8/2009 | Kenny ........................... 239/58 |
| 2009/0302128 A1 | | 12/2009 | Zobele |
| 2009/0311195 A1 | | 12/2009 | Clark et al. |
| 2010/0056422 A1 | | 3/2010 | Lammert et al. |
| 2010/0093531 A1 | | 4/2010 | Habicher et al. |
| 2010/0178042 A1 | | 7/2010 | Neumann et al. |
| 2010/0179099 A1 | | 7/2010 | Loso et al. |
| 2010/0187327 A1 | | 7/2010 | Irvin |
| 2010/0234457 A1 | | 9/2010 | Taranta et al. |
| 2010/0292323 A1 | | 11/2010 | Fujii et al. |
| 2010/0323897 A1 | | 12/2010 | Burke |
| 2011/0010817 A1 | | 1/2011 | Théberge et al. |
| 2011/0114663 A1 | | 5/2011 | Brown et al. |
| 2011/0117156 A1 | | 5/2011 | Lin et al. |
| 2011/0180621 A1 | | 7/2011 | Gruenbacher |
| 2011/0305644 A1 | | 12/2011 | Vijay et al. |

FOREIGN PATENT DOCUMENTS

| | | |
|---|---|---|
| EP | 1319543 | 6/2003 |
| EP | 1698355 | 6/2006 |
| EP | 2055322 | 6/2009 |
| GB | 1514712 | 6/1978 |
| GB | 2380940 | 4/2003 |
| GB | 2407770 | 5/2005 |
| GB | 2407771 | 5/2005 |
| JP | 1991-118749 | 12/1991 |
| JP | 1992-088946 | 8/1992 |
| JP | 1996-112339 | 5/1996 |
| JP | 2004-313637 | 11/2004 |
| WO | 0024434 | 5/2000 |
| WO | 0220172 | 3/2002 |
| WO | 03105652 | 12/2003 |
| WO | 2005044001 | 5/2005 |
| WO | 2005056063 | 6/2005 |
| WO | 2006061803 | 6/2006 |
| WO | 2006128316 | 12/2006 |
| WO | 2007110086 | 4/2007 |
| WO | 2008022477 | 11/2008 |

(56) References Cited

FOREIGN PATENT DOCUMENTS

| WO | 2011030122 | 3/2011 |
| WO | 2011140917 | 11/2011 |
| WO | 2012009386 | 1/2012 |

\* cited by examiner

Fig. 12

VOLATILE MATERIAL DISPENSER AND ITS HOUSING AND CARTRIDGE

TECHNICAL FIELD

The present invention relates to a volatile material dispenser, and the housing and cartridge for the dispenser. More particularly, the present invention relates to a dispenser capable of controlling the dispensing of the volatile material and its housing and cartridge.

BACKGROUND

There are kinds of dispensers in the market that can control the dispensing of the volatile material. In such a dispenser, the volatile material is normally dispensed from a covering plate of a housing. The housing of the dispenser further comprises a regulating plate positioned on the covering plate and movable between an open position and a closed position with respect to the covering plate. Both the covering plate and the regulating plate have bores thereon. The bores of the regulating plate are aligned with the bores of the covering plate when the regulating plate is in the open position so that the volatile material is dispensed through the aligned bores of the regulating plate and the covering plate. The bores of the regulating plates and the covering plates are not aligned with each other when the regulating plate is in the closed position so that the dispensing of the volatile material is inhibited.

Normally, there exists a large or small gap between the regulating plate and the covering plate due to the production process and cost. Therefore, when the dispenser is in the closed position, the gap between bores of the regulating plate and the bores of the covering plate may act as a leakage passage through which the volatile material may be discharged. In the existing dispenser, the bores are distributed relatively uniformly on the covering plate and the regulating plate. Thus, when the dispenser is in the closed position and the bores of the regulating plate are covered by the non-bore portion of the covering plate, the distance between the bores in the regulating plate and the bores in the covering plate adjacent to the bores in the regulating plate is relatively small and the possible gaps therebetween may be distributed all over the covering plate, and therefore there may be a lot of leakage passages in the area between the bores of the regulating plate and those of the covering plate, and the dispensing of the volatile material cannot be inhibited sufficiently. In addition, the travel distance between the open position and closed position of the regulating plate of the existing volatile material dispenser is relative short, and thus the dispensing of the dispenser cannot be regulated finely.

Moreover, in the existing dispenser, the cartridge containing the volatile material is usually movable within the housing of the dispenser. Such movement of the cartridge within the housing may cause certain inconveniencies in the usage.

Therefore, there exists a need to improve the existing volatile material dispenser.

SUMMARY

An object of the present invention is to provide an improved volatile material dispenser that has larger travel distance for regulating, and thus the dispensing of the volatile material in the dispenser can be controlled more precisely. Meanwhile, the dispensing of the volatile material can be substantially inhibited in the closed position of the regulating plate, and the dispenser can retain the cartridge containing the volatile material firmly.

According to one aspect of the present invention, there is provided a housing for a volatile material dispenser, comprising a bottom plate, a covering plate and a chamber defined therebetween for receiving a cartridge containing a volatile material, the cartridge having at least one side that allows the dispensing of the volatile material therefrom, the housing further comprising a regulating plate movably mounted to the covering plate, characterized in that the covering plate and the regulating plate each have one bored portion and one non-bore portion, the bored portion and the non-bore portion of the regulating plate each occupy a half of the regulating plate, the regulating plate is movable between an open position and a closed position with respect to the covering plate, the bored portion of the covering plate is aligned with the bored portion of the regulating plate in the open position, and the bored portion of the covering plate is covered by the non-bore portion of the regulating plate in the closed position, the chamber is provided with a fixing element capable of fixing the cartridge in place.

Since the bored portion and the non-bore portion of the regulating plate are arranged in a concentrated distribution and each of them occupies a half of the regulating plate, the dispenser has reduced number of leakage passages of the volatile material in the chamber, and thus the dispensing of the volatile material can be substantially inhibited when the regulating plate of the dispenser is in the closed position.

Preferably, the regulating plate can be moved to a partially open position between the open position and the closed position, the bored portion of the covering plate is partially covered by the non-bore portion of the regulating plate in the partially open position.

Preferably, the movement of the regulating plate with respect to the covering plate is rotation.

Preferably, the covering plate is provided with an arc-shaped guide slot, and the regulating plate is provided with a tab protruding through the guide slot and movable along the guide slot to adjust the position of the regulating plate with respect to the covering plate.

Preferably, the rotation axis of the regulating plate is at the center of the regulating plate.

Preferably, the circumferential angle of the guide slot with respect to the rotation axis is the same as the circumferential angle of the bored portion of the regulating plate with respect to the rotation axis.

Preferably, the tab is at one end of the guide slot when the regulating plate is in the open position, and the tab is at the other end of the guide slot when the regulating plate is in the closed position.

Preferably, the circumferential angle of the guide slot with respect to the rotation axis is 180 degrees.

Preferably, the non-bore portion of the covering plate has a pattern similar to the pattern of the bored portion of the regulating plate.

Preferably, the fixing element is a post positioned on the bottom plate, the post is adapted to mate with the hole in the cartridge.

Preferably, the fixing element is two curved holders positioned on the bottom plate, and the two curved holders are adapted to mate, respectively, with the contour of the cartridge at opposite sides.

According to another aspect of the present invention, there is provided a cartridge containing volatile material, having at least one side that permits the dispensing of the volatile material therefrom, characterized in that the cartridge is provided with an engagement element that is adapted to mate with a fixing element of the housing of a dispenser.

According to another aspect of the present invention, there is provided a cartridge containing volatile material, having at least one side that permits the dispensing of the volatile material therefrom, characterized in that the cartridge is provided with an engagement element that is adapted to mate with the fixing element of the aforesaid housing of a dispenser.

Preferably, the fixing element of the housing is a post positioned on the bottom plate, and the engagement element of the cartridge is a hole that is adapted to mate with the post of the housing.

Preferably, the fixing element of the housing has two curved holders positioned on the bottom plate, and the engagement element of the cartridge is the curved contours of the cartridge at opposite sides that are adapted to mate, respectively, with the two curved holders of the housing.

According to another aspect of the present invention, there is provided a volatile material dispenser, comprising the aforesaid housing and the aforesaid cartridge disposed in the chamber, the one side of the cartridge faces the covering plate of the housing and the fixing element of the housing is mated with the connecting element of the cartridge.

The advantages of the present invention lie in that the dispensing of the dispenser can be controlled more precisely, the dispensing of the volatile material can be substantially inhibited in the closed position of the regulating plate, and the dispenser can retain the cartridge containing the volatile material firmly.

DETAILED DESCRIPTION

FIGS. 1-4 illustrate a volatile material dispenser 100 according to a preferred embodiment of the present invention. As shown in those figures, the dispenser 100 is in a generally square shape in the elevation view, and comprises a covering plate 300 and a bottom plate 200. The covering plate 300 and the bottom plate 200 are fitted together to define a chamber therebetween for containing the volatile material. The dispenser 100 further comprises a regulating plate 400 rotatably mounted under the covering plate 300. The rotation axis of the regulating plate 400 is substantially at the center of the covering plate 300 and is perpendicular to the covering plate 300.

The covering plate 300 comprises a non-bore portion 310 and a bored portion 320. The non-bore portion 310 does not have any bore, while the bored portion 320 may have any number of bores in various shapes, e.g., in the embodiment shown in the aforesaid figures, the bored portion 320 has two bores 321 and 322. The regulating plate 400 also comprises a non-bore portion 410 and a bored portion 420. The non-bore portion 410 does not have any bore, while the bored portion 420 may have any number of bores in various shapes, such as bores 421. The bored portion and the non-bore portion of the covering plate 300 and the regulating plate 400 are arranged in a concentrated distribution. The term "concentrated distribution" means that each of the bored portion and the non-bore portion occupies a considerably large area, such as ½ or ¼ of the covering plate 300 or the regulating plate 400. In the embodiment shown in FIGS. 1-4, the bored portion 320 and the non-bore portion 310 are generally divided by a diagonal line extending from the upper left corner to the lower right corner of the covering plate 300, wherein the bored portion 320 is located at the lower left of the covering plate 300, while the non-portion 310 located at the upper right of the covering plate 300. In the embodiment shown in FIGS. 1-4, the bored portion 420 and the non-bore portion 410 of the regulating plate 400 are divided by a straight line extending through the rotation center of the regulating plate 400, each substantially occupies a half of the regulating plate 400.

Figure 1:
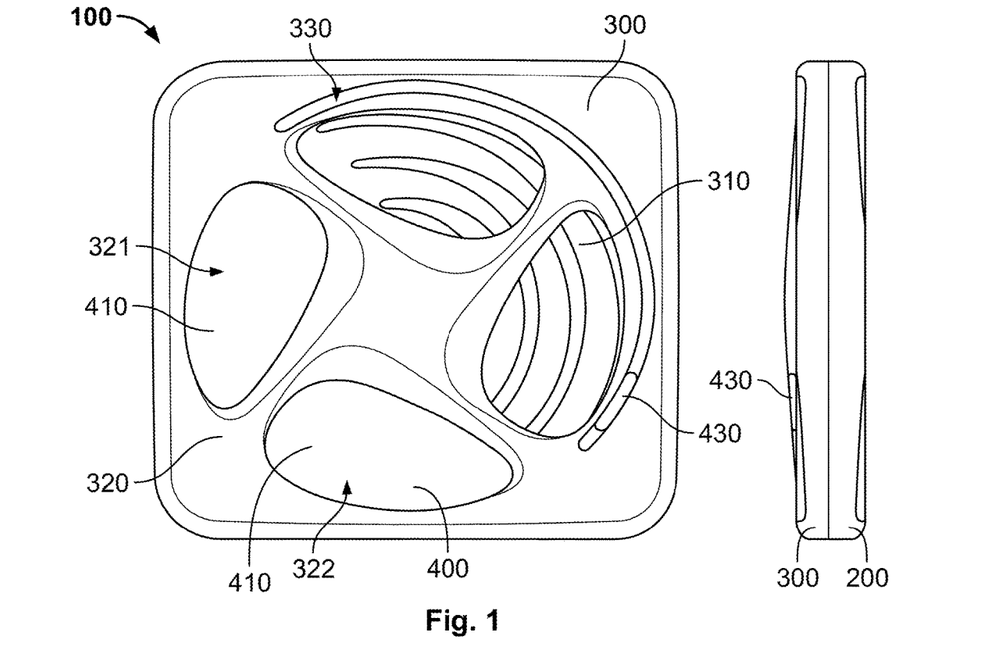
FIG. 1 illustrates an elevation view and a right elevation view of the volatile material dispenser according to a preferred embodiment of the present invention, in which the regulating plate is in the closed position.
Figure 2:
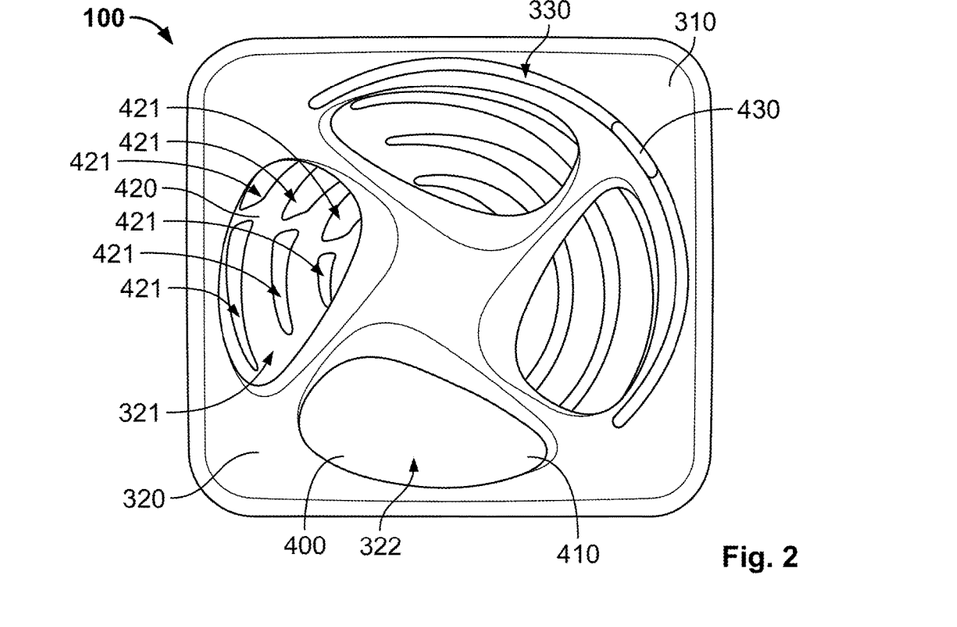
FIG. 2 illustrates an elevation view of the volatile material dispenser of FIG. 1 in the partially open position.
Figure 3:
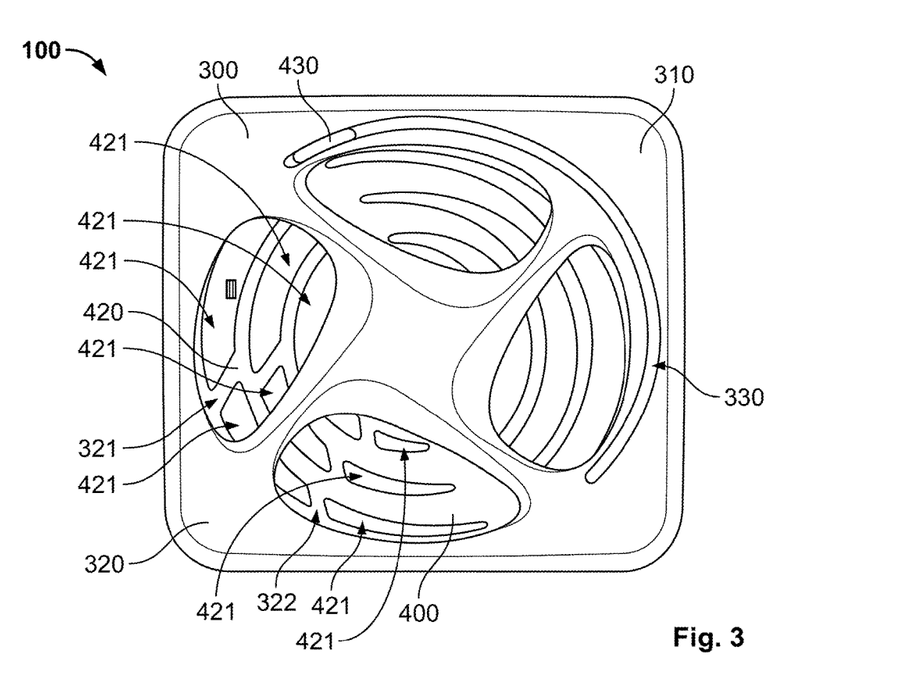
FIG. 3 illustrates an elevation view of the volatile material dispenser of FIG. 1 in the open position.
Figure 4:
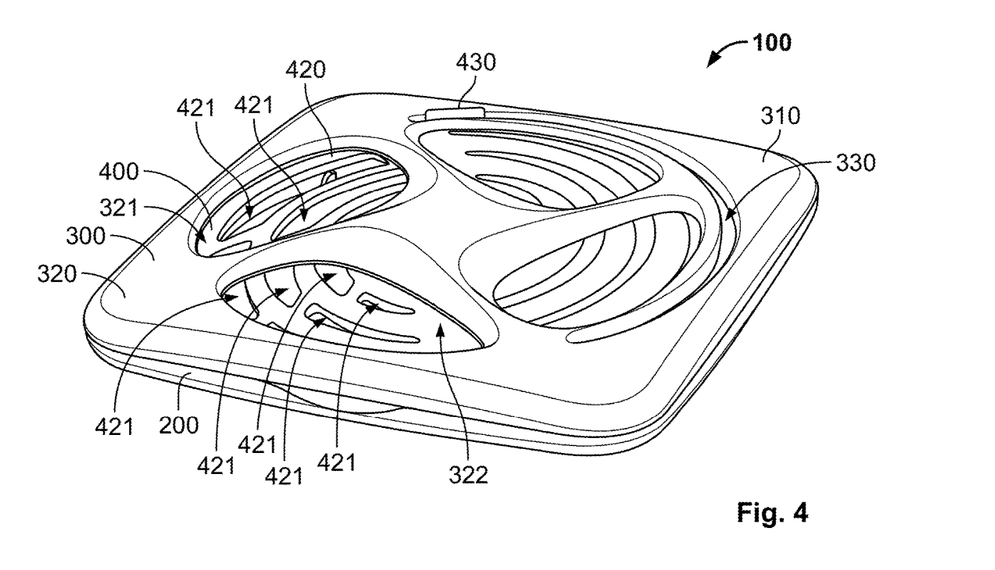
FIG. 4 illustrates a perspective view of the volatile material dispenser of FIG. 1.

The covering plate 300 further comprises an arc-shaped guide slot 330 positioned outside the non-bore portion 310 and extending around the rotation axis of the regulating plate. The regulating plate 400 comprises a tab 430 extending out through the guide slot 330. The regulating plate 400 rotates around its rotation axis between the open position and the closed position with respect to the covering plate 300 when the tab 430 is moved by a user along the guide slot 330. In the position as shown in FIG. 1, the regulating plate 400 is in the closed position in which the bored portion 420 of the regulating plate 400 is covered by the non-bore portion 310 of the covering plate 300, while the bored portion 320 of the covering plate 300 is also covered by the non-bore portion 410 of the regulating plate 400. Therefore, all the bores of the regulating plate 400 are covered when the regulating plate 400 is in the closed position, and thus the volatile material in the chamber cannot be dispensed through the regulating plate 400. In the position as shown in FIG. 3, the regulating plate 400 is in the open position, wherein the bored portion 420 of the regulating plate 400 is aligned with the bored portion 320 of the covering plate 300. Therefore, when the regulating plate 400 is in the open position, the volatile material in the chamber can be dispensed through the bores of the regulating plate 400. In the position as shown in FIG. 2, the regulating plate 400 is in a partially open position between the open position and the closed position. When the regulating plate 400 is in the partially open position, a portion of the bored portion 420 of the regulating plate 400 is covered by the non-bore portion 310 of the covering plate 300, and the remainder of the bored portion 420 is aligned with the bored portion 320 of the covering plate 300. When the regulating plate 400 is in a partially open position, the dispensing rate of the volatile material is also between those in the open position and the closed position because the bored portion 420 is partially shielded. The alignment between the bored portion 420 and the bored portion 320 can be regulated by altering the position of the tab 430 within the guide slot 330 so as to adjust the dispensing rate of the volatile material. In the embodiment as shown in FIGS. 1-4, the circumferential angle of the guide slot 330 with respect to the rotation axis of the regulating plate 400, i.e., the angle between the two lines from the rotation center of the regulating plate to the opposite ends of the guide slot, is about 180 degrees. Therefore, the travel distance of the tab 430 is relatively large, and thus the dispensing level of the dispenser can be regulated accurately.

Figure 5:
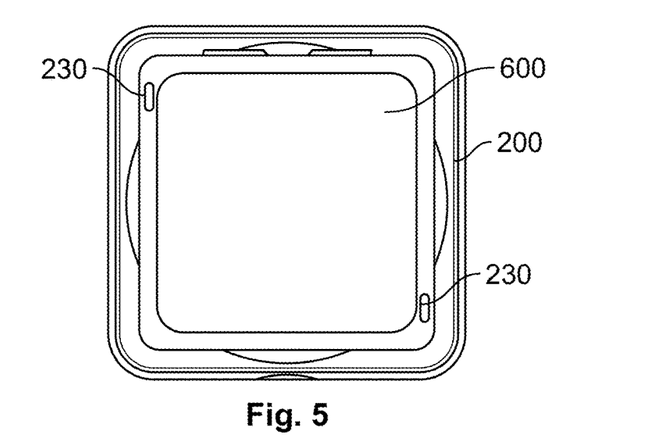
FIGS. 5-7 illustrate an elevation view, a perspective view and an exploded perspective view of the volatile material dispenser of FIG. 1, wherein the covering plate is removed to show the interior structure.
Figure 6:
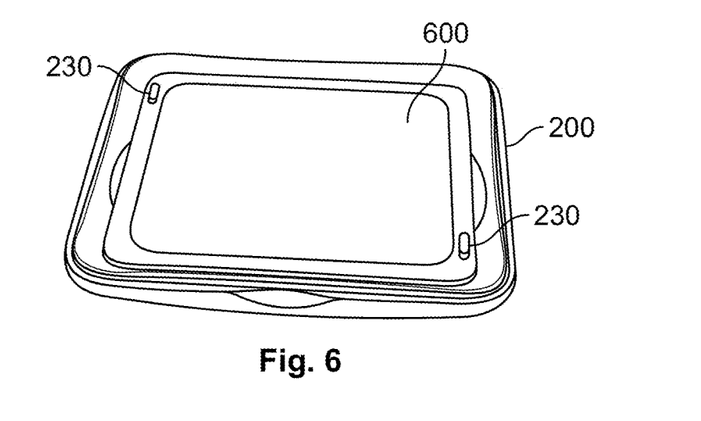
Figure 7:
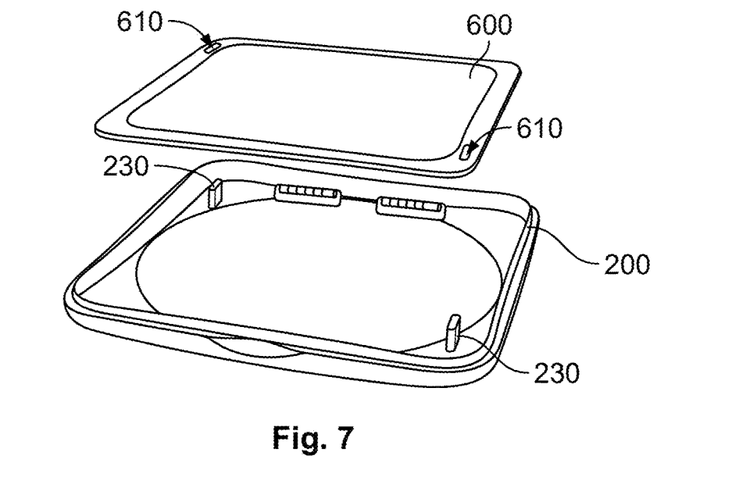

FIGS. 5-7 illustrate the interior structure of one embodiment of the present invention. As clearly shown in FIG. 7, the bottom plate 200 comprises two retaining posts 230 extending upwardly from two generally diagonal positions of the bottom plate 200, and the cartridge 600 has holes 610 provided at two corresponding positions. As shown in FIGS. 5-6, the two retaining posts 230 on the bottom plate 200 extend through the two holes 610 in the cartridge 600 respectively to retain the cartridge 600 in place when the cartridge 600 is mounted on the bottom plate 200.

Figure 8:
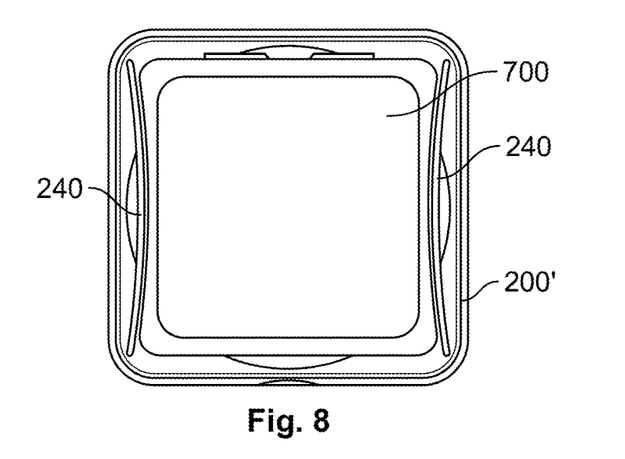
FIGS. 8-10 illustrate an elevation view, a perspective view and an exploded perspective view of the volatile material dispenser according to an alternative embodiment, wherein the covering plate is removed to show the interior structure.
Figure 9:
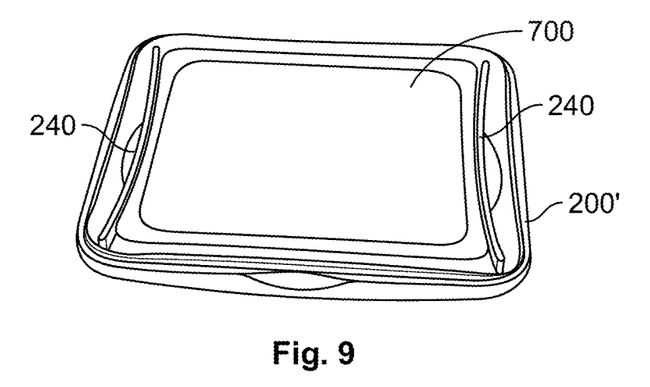
Figure 10:
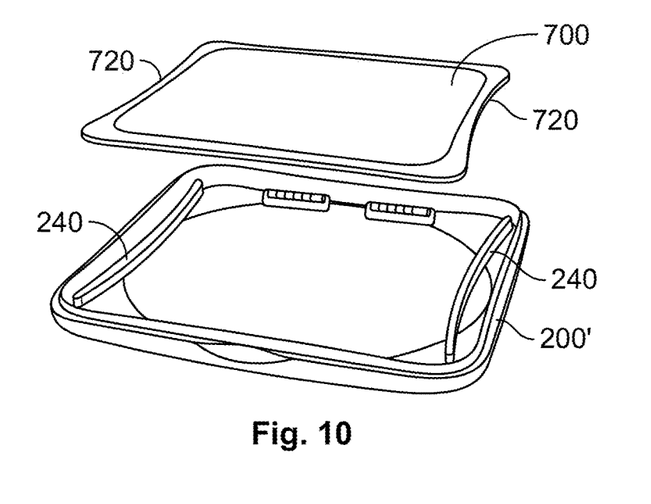
Figure 11:
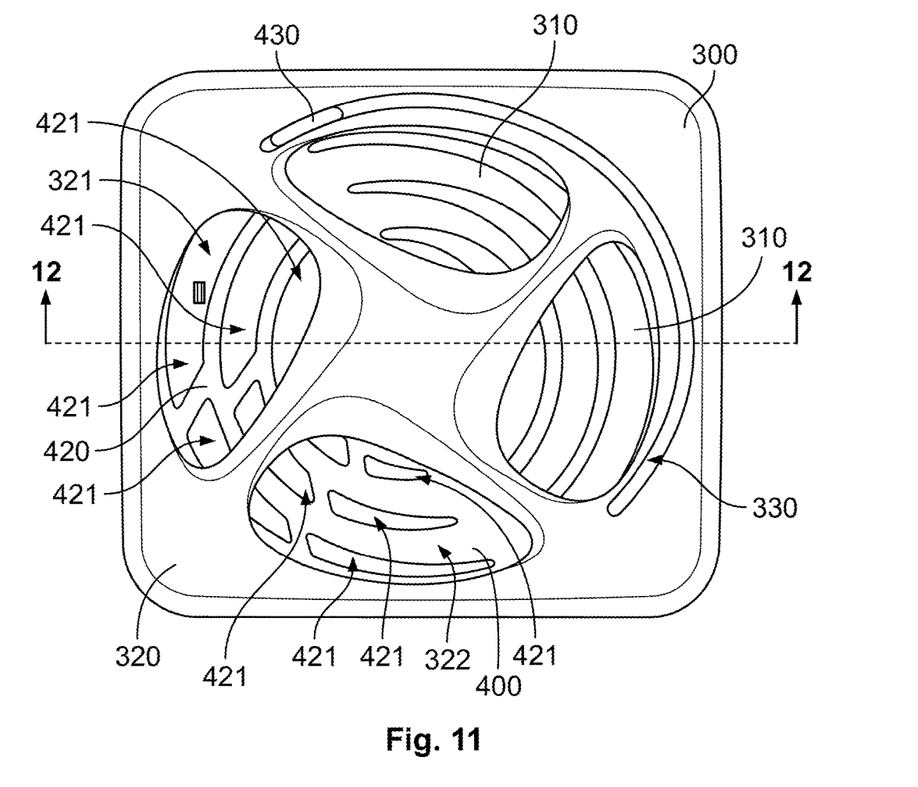
FIG. 11 illustrates an elevation view of the volatile material dispenser of FIG. 1 in the open position.
Figure 12:
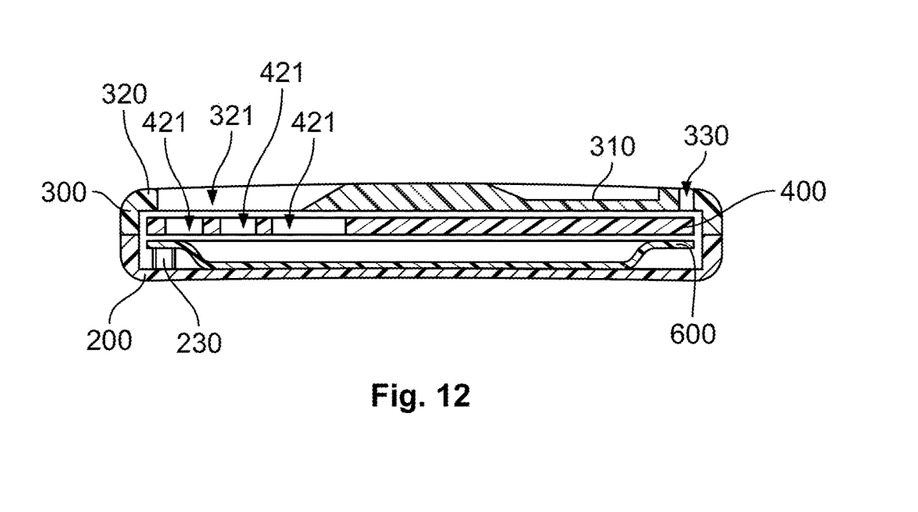
FIG. 12 illustrates a cross-sectional view of the volatile material dispenser of FIG. 11 in the open position along the line 12-12 thereof.

FIGS. 8-10 illustrate the interior structure of one embodiment of the present invention. As clearly shown in FIG. 10, the bottom plate 200' includes curved holders 240 positioned at both the left and right sides of the bottom plate 200'. Meanwhile, the contours 720 at the left and right sides of the cartridge 700 are adapted to mate with the contours of the inner sides of the curved holders 240. As shown in FIGS. 8-9, the two curved holders 240 on the bottom plate 200' retain the contours 720 of the left and right sides of the cartridge 700 from both the left and right sides to retain the cartridge 700 in place.

Although FIGS. 1-10 illustrate preferred embodiments of the present invention, a person skilled in the art will understand that the present invention may have various alternative embodiments.

In the preferred embodiments, both the covering plate and the regulating plate have one bored portion and one non-bore portion, each occupies a half of the covering plate or regulating plate. However, the present invention is not limited thereto, and the covering plate and the regulating plate may have any number of bored portions and non-bored portions with various dimensions. In an alternative embodiment, each of the covering plate and the regulating plate has two bored portions and two non-bore portions, the bored portion and the non-bore portion are disposed alternately, each occupies about ¼ of the covering plate or the regulating plate.

In an alternative embodiment, the rotation axis of the regulating plate may not be positioned at the center of the covering plate. In one alternative embodiment, the rotation axis of the regulating plate is located at one corner of the covering plate. In such a case, the dispenser may appear to be a generally circular sector, and the rotation axis of the regulating plate is located at the circle center of the circular sector.

In an alternative embodiment, the rotation axis may not be positioned within the dispenser, but may be positioned outside the dispenser. In such a case, the dispenser may appear to be a ring segment. In such a case, there may be two guide slots and two tabs disposed in the two slots respectively. The two guide slots may be disposed near the largest diameter and the smallest diameter of the ring segment respectively.

In an alternative embodiment, the regulating plate may not rotate relative to the covering plate, but may move in a straight line with respect to the covering plate. In such a case, the guide slot may be straight.

In an alternative embodiment, the regulating plate may be disposed on the covering plate. The guide slot is not necessary in such a case. In an alternative embodiment, the dispenser may not include a tab and a slot, and the regulating plate may be moved relative to the covering plate by other means known in the art.

In an alternative embodiment, the dispenser may have various shapes. For example, the dispenser may not appear to be a generally square in an elevation view, but may appear to be a circle, a rectangle or an ellipse, etc. The dispenser may not appear to be in a flat shape as shown in the drawings, and the dispenser may have an increased thickness to achieve a chamber having a larger volume.

In the preferred embodiment, the dispenser is made of plastic. However, the dispenser may be made of various materials, such as metal. The components of the dispenser may be made of different materials.

In the preferred embodiment, the fixing element on the housing of the dispenser has retaining posts or curved holders provided on the bottom plate, and the engaging portion on the cartridge has holes or contours of the cartridge at the sides adapted to mate with the retaining posts or curved holders. However, the present invention is not limited thereto, and the fixing element may be provided on the covering plate, and there may be any number of retaining posts positioned at any appropriate positions, as long as the retaining posts can mate with the holes of the cartridge so as to retain the cartridge in place. In the embodiment of FIGS. 8-10, the fixing element has inwardly curved holders disposed at opposite two sides. However, the present invention is not limited thereto, and the holders may be disposed at more than two sides, and the fixing element may have holder(s) in any appropriate shape, as long as the holder(s) can mate with the contour of the cartridge, so as to retain the cartridge in plate.

The above only describes several specific embodiments of the present invention, and a person skilled in the art will appreciate that modifications and improvements can occur without departing from the spirit of the present invention. All such modifications and improvements fall within the scope of the present invention defined by the following claims.

The invention claimed is:

1. A housing for a volatile material dispenser, comprising a bottom plate, a covering plate non-rotatingly fitted to the bottom plate and provided with a guide slot, and a chamber defined therebetween for receiving a cartridge containing a volatile material, the cartridge having at least one side that allows dispensing of the volatile material therefrom, the housing further comprising a regulating plate positioned within the chamber and movably mounted to the covering plate, the regulating plate positioned directly and entirely above the cartridge when the cartridge is positioned within the chamber, the regulating plate also including a tab protruding through the guide slot and movable along the guide slot, characterized in that both the covering plate and the regulating plate each have one bored portion and one non-bore portion, the bored portion and the non-bore portion of the regulating plate each occupy a half of the regulating plate, the regulating plate is movable between an open position and a closed position with respect to the covering plate, the bored portion of the covering plate is aligned with the bored portion of the regulating plate in the open position, and the bored portion of the covering plate is covered by the non-bore portion of the regulating plate in the closed position, the regulating plate is rotatably adjusted relative to the covering plate by moving the tab within the guide slot, the chamber defines a single open cavity and includes a fixing element capable of fixing the cartridge in place.

2. The housing of the dispenser of claim 1, characterized in that the regulating plate can be moved to a partially open position between the open position and the closed position, wherein the bored portion of the covering plate is partially covered by the non-bore portion of the regulating plate in the partially open position.

3. The housing of the dispenser of claim 2, characterized in that the movement of the regulating plate with respect to the covering plate is rotational.

4. The housing of the dispenser of claim 3, characterized in that the rotation axis of the regulating plate is at the center of the regulating plate.

5. The housing of the dispenser of claim 4, characterized in that the circumferential angle of the guide slot with respect to the rotation axis is the same as the circumferential angle of the bored portion of the regulating plate with respect to the rotation axis.

6. The housing of the dispenser of claim 5, characterized in that the tab is at one end of the guide slot when the regulating plate is in the open position, and the tab is at the other end of the guide slot when the regulating plate is in the closed position.

7. The housing of the dispenser of claim 5, characterized in that the circumferential angle of the guide slot with respect to the rotation axis is 180 degrees.

8. The housing of the dispenser of any one of claims 1-3 or 4-7, characterized in that the non-bore portion of the covering plate has a pattern similar to the pattern of the bored portion of the regulating plate.

9. The housing of the dispenser of any one of claims 1-3 or 4-7, characterized in that the fixing element is a post positioned on the bottom plate, and the post is adapted to mate with a hole in the cartridge.

10. The housing of the dispenser of any one of claims 1-3 or 4-7, characterized in that the fixing element has two curved holders positioned on the bottom plate, and the two curved holders are adapted to mate, respectively, with a first contour and a second contour of the cartridge, the first and second contours of the cartridge being at opposite sides of the cartridge.

11. The housing of the dispenser of claim 1, the fixing element of the housing has a first curved holder positioned at a first side of the bottom plate of the housing and a second curved holder positioned at a second side of the bottom plate opposite the first side of the bottom plate, the first curved holder and the second curved holder being adapted to mate, respectively, with a first curved contour and a second curved contour of the cartridge.

12. The housing of the dispenser of claim 1, characterized in that the fixing element of the housing has a first post and a second post, the first and second posts extending upwardly from two diagonal positions of a bottom plate of the housing, the first and second posts on the bottom plate adapted to extend through first and second holes, respectively, each arranged within a periphery of the cartridge to retain the cartridge in place when the cartridge is mounted on the bottom plate.

13. The housing of the dispenser of claim 11, wherein the first and second curved holders curve inward toward each other.

14. The housing of the dispenser of claim 11, wherein the bottom plate further includes a third side and a fourth side connecting the first side and the second side, the third and fourth sides each having a linear profile.

15. The housing of the dispenser of claim 12, wherein the-bottom plate has a generally square shape, the first post being positioned proximate a first corner of the bottom plate, and the second post being positioned proximate a second corner of the bottom plate diagonally opposite the first corner.

16. The housing of the dispenser of claim 1, wherein the bottom plate defines a continuous inner surface.

17. The housing of the dispenser of claim 16, wherein the continuous inner surface is arranged within a wall extending around a periphery of the bottom plate.

18. The housing of the dispenser of claim 12, wherein the two diagonal positions of the bottom plate are arranged adjacent to a wall extending around a periphery of the bottom plate.

19. The housing of the dispenser of claim 1, wherein the fixing element includes a plurality of posts extending upwardly from the bottom plate.

20. The housing of the dispenser of claim 19, wherein one or more of the plurality of posts are configured to extend through one or more holes corresponding to the plurality of posts.

21. A housing for a volatile material dispenser, comprising: a bottom plate; a covering plate non-rotatingly fitted to the bottom plate and provided with a guide slot; a chamber defined between the covering plate and the bottom plate for receiving a cartridge containing a volatile material, the cartridge having at least one side that allows dispensing of the volatile material therefrom; and a regulating plate positioned within the chamber and movably mounted to the covering plate, the regulating plate positioned directly and entirely above the cartridge when the cartridge is positioned within the chamber, the regulating plate also including a tab protruding through the guide slot and movable along the guide slot, both the covering plate and the regulating plate each have at least one bored portion and at least one non-bore portion, the regulating plate is movable between an open position and a closed position with respect to the covering plate, the at least one bored portion of the covering plate is aligned with the at least one bored portion of the regulating plate in the open position, and the at least one bored portion of the covering plate is covered by the at least one non-bore portion of the regulating plate in the closed position, the regulating plate is rotatably adjusted relative to the covering plate by moving the tab within the guide slot.

* * * * *